United States Patent
Kreck et al.

(10) Patent No.: US 7,096,750 B2
(45) Date of Patent: Aug. 29, 2006

(54) SEQUENCING AND AVERAGING MULTIPLE SAMPLE SYSTEM

(75) Inventors: Jeffrey Weston Kreck, Carson City, NV (US); Robert Terrance Daniel, Reno, NV (US); Theodore Robert Barben, II, Carson City, NV (US)

(73) Assignee: Universal Analyzers, Inc., Carson City, NV (US)

( * ) Notice: Subject to any disclaimer, the term of this patent is extended or adjusted under 35 U.S.C. 154(b) by 70 days.

(21) Appl. No.: 10/819,659

(22) Filed: Apr. 6, 2004

(65) Prior Publication Data
US 2005/0217351 A1    Oct. 6, 2005

(51) Int. Cl.
*G01N 1/16* (2006.01)
(52) U.S. Cl. .................. 73/863.33; 73/64.56
(58) Field of Classification Search ............... None
See application file for complete search history.

(56) References Cited

U.S. PATENT DOCUMENTS

| | | |
|---|---|---|
| 4,161,988 A | 7/1979 | Hart |
| 4,325,910 A | 4/1982 | Jordan |
| 4,836,038 A | 6/1989 | Baldwyn |
| 5,835,541 A | 11/1998 | Namekata et al. |
| 6,167,766 B1 | 1/2001 | Dunn et al. |
| 6,592,827 B1 | 7/2003 | Zilker, Jr. et al. |

*Primary Examiner*—Hezron Williams
*Assistant Examiner*—Paul M. West
(74) *Attorney, Agent, or Firm*—Thorpe, North & Western, LLP

(57) ABSTRACT

Apparatus and methods are provided for testing and analyzing a plurality of stream sources to monitor for an upset condition in one of the stream sources. A manifold is provided having a plurality of manifold inlets and a manifold outlet. A plurality of sampling devices for sampling the plurality of stream sources are coupled to the manifold inlets to provide stream samples to the manifold. A controller is in electronic communication with each of the plurality of sampling devices for providing test samples in the manifold. The controller alternately operates the sampling devices in (1) a sequencing mode in which each test sample is a stream sample from one of the plurality of sampling devices or (2) an averaging mode in which each test sample is representative of an average of the stream samples from the plurality of sampling devices. An analyzer is coupled to the manifold outlet to receive the test samples from the manifold and analyze each test sample for the presence of the upset condition.

29 Claims, 6 Drawing Sheets

SEQUENCING AND AVERAGING MULTIPLE SAMPLE SYSTEM

BACKGROUND

1. Field of Invention

The present disclosure relates to sampling methods and apparatus, and more particularly to sequencing and averaging multiple sampling methods and systems.

2. Prior Art

Continuous online analysis of components in liquid and gas streams is a common practice in industry today. For example, routine sampling and analysis is conducted in power plant smokestacks, liquid waste streams, industrial process streams, the head space in storage vessels and many other sources. Because analytical monitors and instrumentation are quite expensive, it is often desirable to share an analyzer bank with multiple sample streams. This is usually accomplished by one of two methods—sequencing or averaging.

In sequencing, the analyzer tests each sample in sequence, on a time share basis. A controller or multiplexer system may utilize a programmable logic controller (PLC), distributed control system (DCS) or a computer to sequence through multiple sample chambers, each obtaining samples via valve-controlled orifices. An example of a sequencing sampling system in shown in U.S. Pat. No. 4,325,910 (Jordan). Averaging systems involve feeding multiple input samples into a central manifold or header and mixing the samples prior to analyzing the mixture. A control device, such as a needle valve, is used to precisely control the flow of each sample into the manifold. The combined mixture is then analyzed to provide an average reading for all of the samples.

Either of the above two methods works fairly well in the absence of an upset condition. However, when a problem arises with one of the sampled streams, both prior art systems have difficulty in quickly locating the stream that is out of specification. In the case of sequencing, the upset condition will not be detected during the time that the analyzer is testing other samples. If the streams being analyzed are potent, toxic, flammable, radioactive or otherwise dangerous, the delay in detecting an upset condition could have serious consequences. An averaging system could also involve a substantial delay in finding an upset condition, because the samples are all mixed before being analyzed. Moreover, it may be difficult to even detect the presence of a problem sample because each sample is substantially diluted with other samples before being analyzed. Accordingly, new methods and apparatus are needed to quickly and accurately locate an upset condition in a stream flow using a multiple stream analyzer.

SUMMARY

In a first embodiment of the present disclosure, apparatus is provided for testing and analyzing a plurality of stream sources to monitor for an upset condition in one of the stream sources. A manifold is provided having a plurality of manifold inlets and a manifold outlet. A plurality of sampling devices for sampling the plurality of stream sources are coupled to the manifold inlets to provide stream samples to the manifold. A controller is in electronic communication with each of the plurality of sampling devices for providing test samples to the manifold. The controller alternately operates the sampling devices in (1) a sequencing mode in which each test sample is a stream sample from one of the plurality of sampling devices or (2) an averaging mode in which each test sample is representative of an average of the stream samples from the plurality of sampling devices. An analyzer is coupled to the manifold outlet to receive the test samples from the manifold and analyze each test sample for the presence of the upset condition.

In another embodiment of the present disclosure, a method is provided for testing and analyzing a plurality of stream sources having various flow rates or velocities to monitor for an upset condition in one of the stream sources. A plurality of samples are provided from the plurality of stream sources using a plurality of sampling devices coupled to a manifold. A controller electronically communicates with the plurality of sampling devices to provide test samples to the manifold, alternately operating in (1) a sequencing mode in which each test sample is a stream sample from one of the plurality of sampling devices or (2) an averaging mode in which each test sample is representative of an average of the stream samples from the plurality of sampling devices. The test samples are analyzed using an analyzer coupled to the manifold to determine the presence of the upset condition.

BRIEF DESCRIPTION OF THE DRAWINGS

The above-mentioned features and other features and advantages of this disclosure will become more apparent and the disclosure will be better understood by reference to the following description of an exemplary implementation taken in conjunction with the accompanying drawings, wherein.

Throughout the drawings, identical reference numbers may designate similar, but not necessarily identical, elements. The examples herein illustrate selected implementations of the disclosure in certain forms, and such exemplification is not to be construed as limiting the scope of the disclosure in any manner.

DETAILED DESCRIPTION

The embodiments described herein provide unique apparatus and methods for analyzing samples of various industrial sources, using a combination of sequencing and averaging methods to determine the presence of an upset condition in one or more of the sources. As used herein, the term "upset condition" refers to the sensing of one or more parameters in a source being monitored to determine the presence, absence, excessive amount or deficient amount in a quantity that deviates from a pre-selected standard by an unacceptable amount. Examples could be excessive amounts of contaminants, the presence of unacceptable toxic elements, or the absence of beneficial elements.

The apparatus and methods disclosed herein utilize the same hardware to carry out both the sequencing and the averaging methods, relying on software or programmed firmware to vary the sequencing and/or averaging processes, as needed. By utilizing both sequencing and averaging, the delay time in finding an upset condition is minimized, thereby lessening the possibility of damage to the related equipment, exceeding regulated standards or causing health-threatening conditions. Moreover, the use of the same apparatus for both sequencing and averaging methods substantially reduces monitoring costs, space requirements and maintenance.

The sequencing and averaging multiple sample system of the present invention is useful in monitoring a wide variety of industrial sources and processes. For example, the present system may be used to monitor exhaust gas flow from turbines or boilers, measuring oxygen or carbon monoxide output to control the fuel and air mixture in the burners. Combustion output may also be monitored to insure that products of combustion, such as sulfur oxides, nitrogen oxides, mercury, carbon monoxide, hydrochloric acid and hydrofluoric acid, are within prescribed limits. Liquid flow may also be monitored in a series of process streams to measure pH or to determine the level of toxic waste. In solid processes, coal conveyer belts may be monitored to sense the presence of carbon monoxide, indicating a fire that must be extinguished. Storage vessels and the head space in storage vessels, as well as many other sources may also be monitored and analyzed with the present system.

Figure 1:
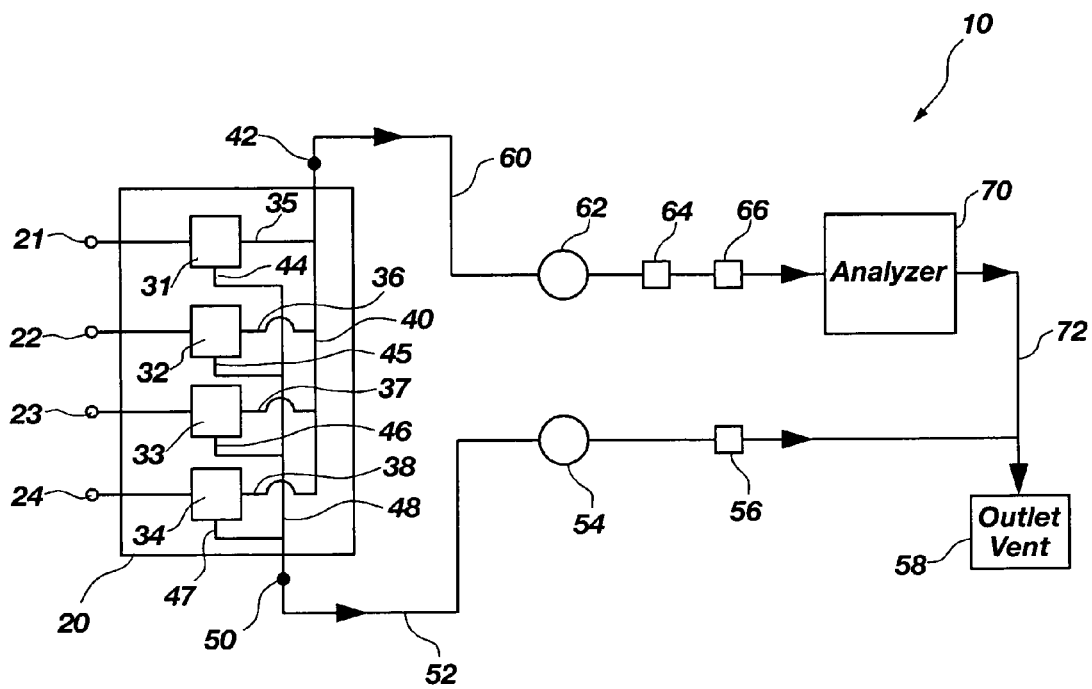
FIG. 1 is a schematic diagram showing the fluid flow arrangement of the sequencing and averaging apparatus according to an embodiment of the present invention.

Referring now to FIG. 1, a schematic diagram discloses a simplified fluid flow arrangement according to an embodiment of the present invention. A manifold 20, disposed within an enclosure (not shown), is adjacent to four fluid sample input connections 21–24. Four three-way valves 31–34 each connect to one of ports 21–24. Valves 31–34 each have output ports 35–38 that feed into the enclosure of manifold 20. An output line 40 provides a sample in manifold 20 to sample outlet connection 42.

Each of valves 31–34 also have constant flow ports 44–47 that are coupled to a common bypass line 48 which is connected to a bypass outlet connection 50. Bypass line 52 is powered by a fluid pump 54 and checked by a flow meter 56 before being shunted to an output vent 58. Likewise, a sample line 60 is coupled to sample outlet 42 and runs to a fluid pump 62, a filter 64 and a flow meter 66 in series. The fluid sample in line 60 flows from flow meter 66 to an analyzer 70, used for monitoring various parameters, as discussed above. An output line 72 also flows to output vent 58.

Thus, as shown in FIG. 1, fluid flow samples are provided on input ports 21–24 from external sources (not shown). The three way valves 31–34 provide the samples into the manifold, where they are mixed (if in the averaging mode), the result test sample is sensed and is provided to the analyzer for the appropriate monitoring. The valves 31–34 may be mounted on the manifold 20 or disposed to stand alone.

Figure 2:
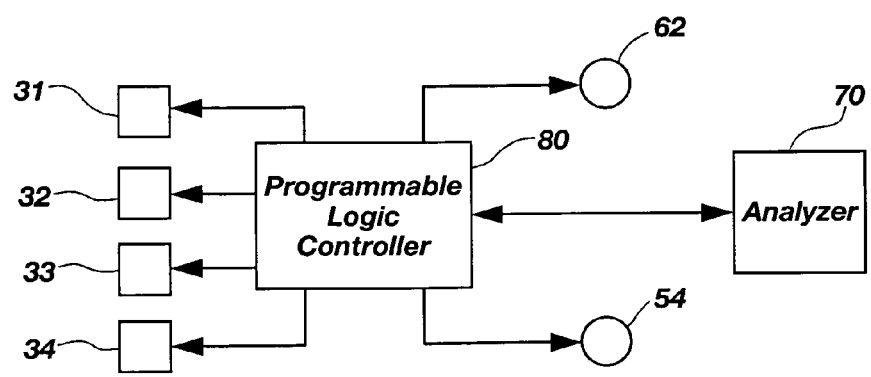
FIG. 2 is a schematic diagram showing the electrical control arrangement of the sequencing and averaging apparatus according to the embodiment shown in FIG. 1.

FIG. 2 is a related schematic diagram showing the electrical control connections of the embodiment shown in FIG. 1. Valves 31–34 are each connected to and controlled by a programmable logic controller 80, which also drives fluid pumps 54 and 62. Pumps 54 and 62 may be a common pump device with two heads driving the bypass line 52 and the sample line 60. Programmable logic controller 80 is connected to analyzer 70 to interrelate functions between controller 80 and analyzer 70, as needed.

Figure 4:
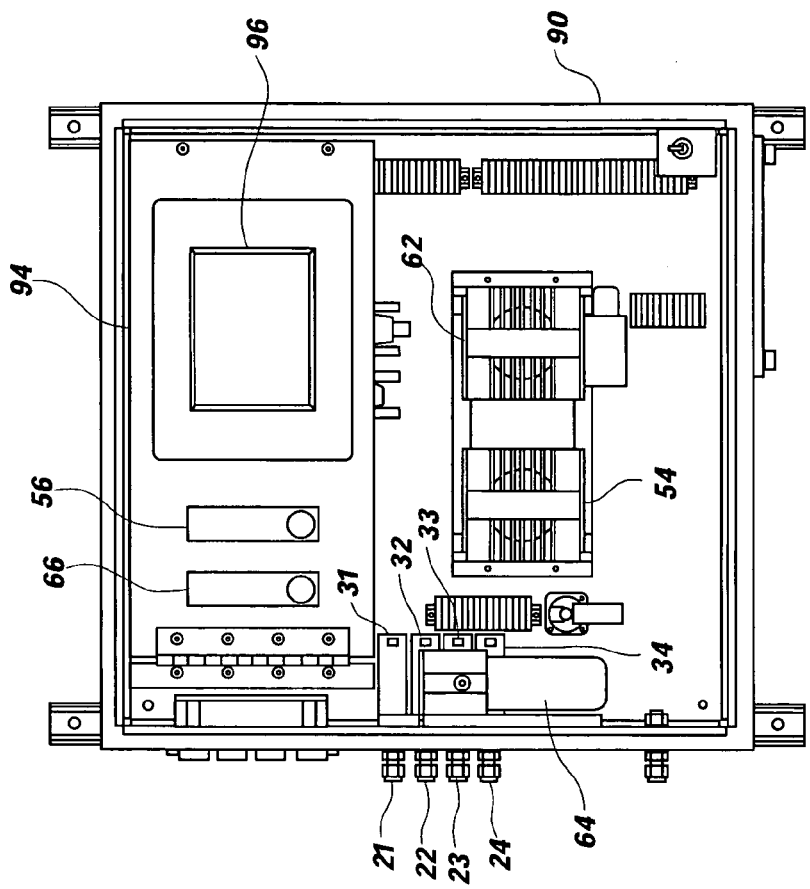
FIGS. 3 and 4 are plan drawings showing the sequencing and averaging apparatus according to the embodiment shown in FIG. 1.
Figure 3:
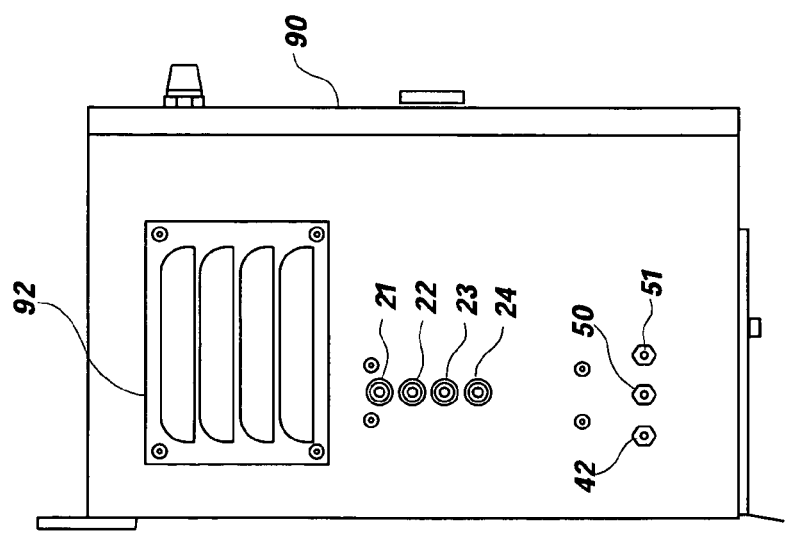

FIGS. 3 and 4 show side and front views, respectively, of an enclosure 90 that houses the sequencing and averaging system of the present embodiment. In FIG. 3, enclosure 90 includes sample inlet connections 21–24. Sample output connection 42 is disposed near the bottom of enclosure 90, adjacent to bypass outlet connection 50 and an atmospheric bleed connection 51. A louvered fan vent 92 is also provided at the side of enclosure 90.

FIG. 4 shows the front of enclosure 90 with a front door (not shown) removed. Sample inlet connections 21–24 are shown connecting to valves 31–34. Fluid pumps 54 and 62 and filter 64 are mounted in the enclosure 90. Flow meters 56 and 66 are mounted on an inner door 94 having a touch panel view window 96. The programmable logic controller 80 (not shown) is mounted within enclosure 90 behind inner door 94.

The analyzer 70 (not shown) may be also be located within enclosure 90 or at some location remote from enclosure 90 and in communication with manifold 20 and programmable logic controller 80. Analyzer 70 may be a convention analyzer such as model number Ultramat 23 made by Siemens. Programmable logic controller 80 may by a conventional controller such as model number 06 made by Automation Direct.

Figure 5:
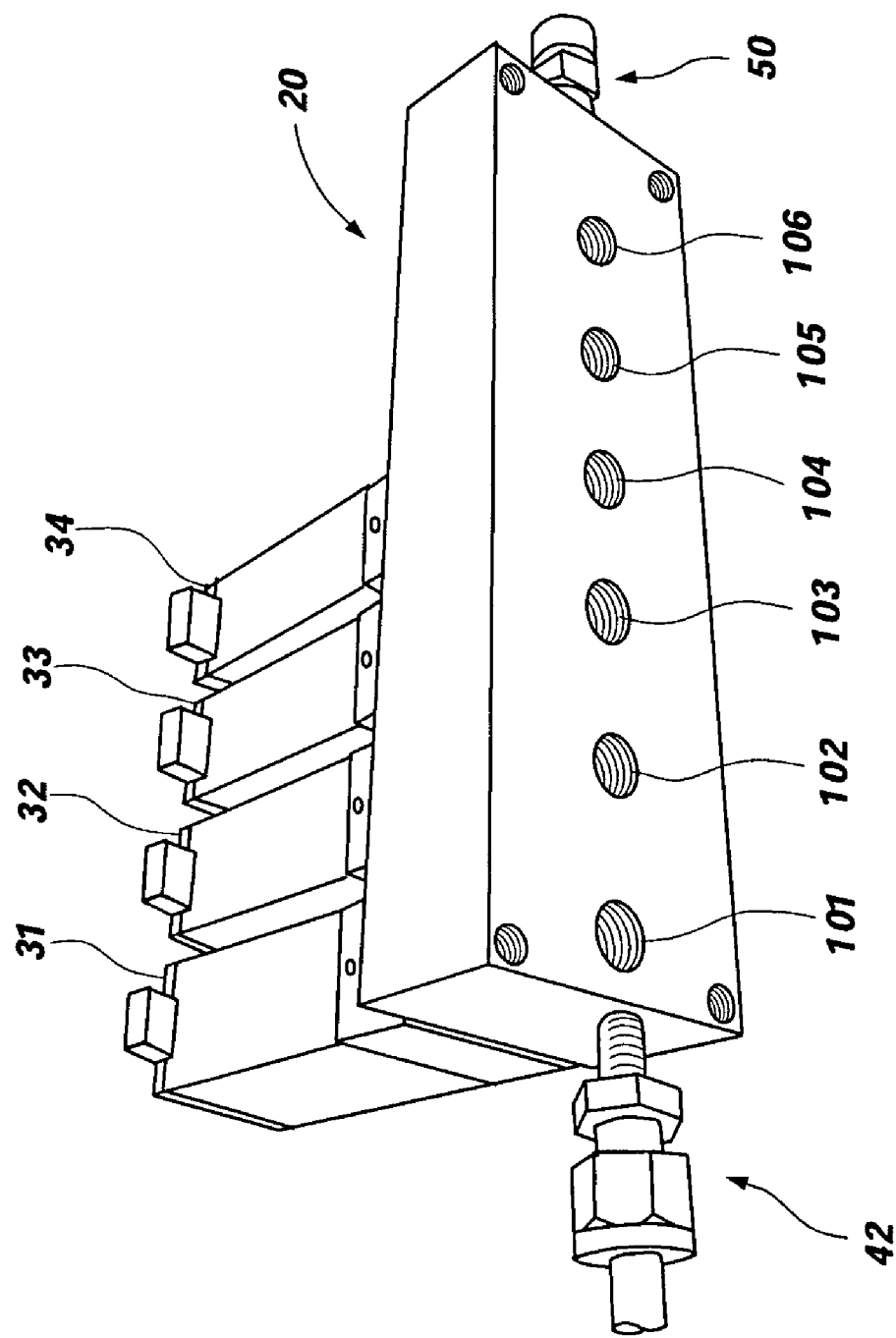
FIG. 5 is a perspective view of manifold and valve apparatus according to the embodiment shown in FIG. 1.

FIG. 5 shows a perspective view of manifold 20 having openings 101–106 to accommodate six solenoid valves. The four three-way valves 31–34 are shown. The valves may be high-speed three-way solenoid valves, such as Type 6608 analytical solenoid valves made by Burkert Controlmatic USA in Irvine, Calif. Any number of valves may be mounted on a convention manifold or header, as needed. Outlet sample connection 42 and bypass connection 50 are also shown. Manifold 20 may be a convention manifold having chamber volume ranging from 5 ml to 100 ml, with 10 ml being a typical volume.

Figure 6:
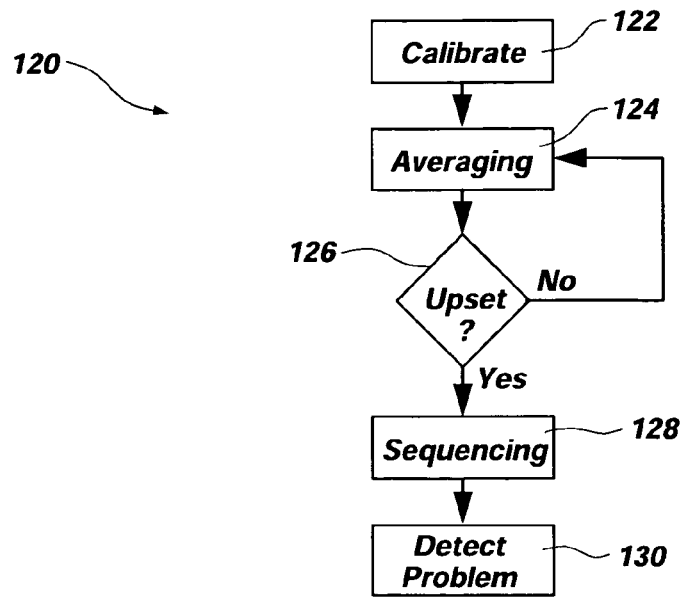
FIGS. 6, 7, 8 and 9 are flow diagrams showing methods of the sequencing and averaging apparatus according to the embodiment shown in FIG. 1.
Figure 7:
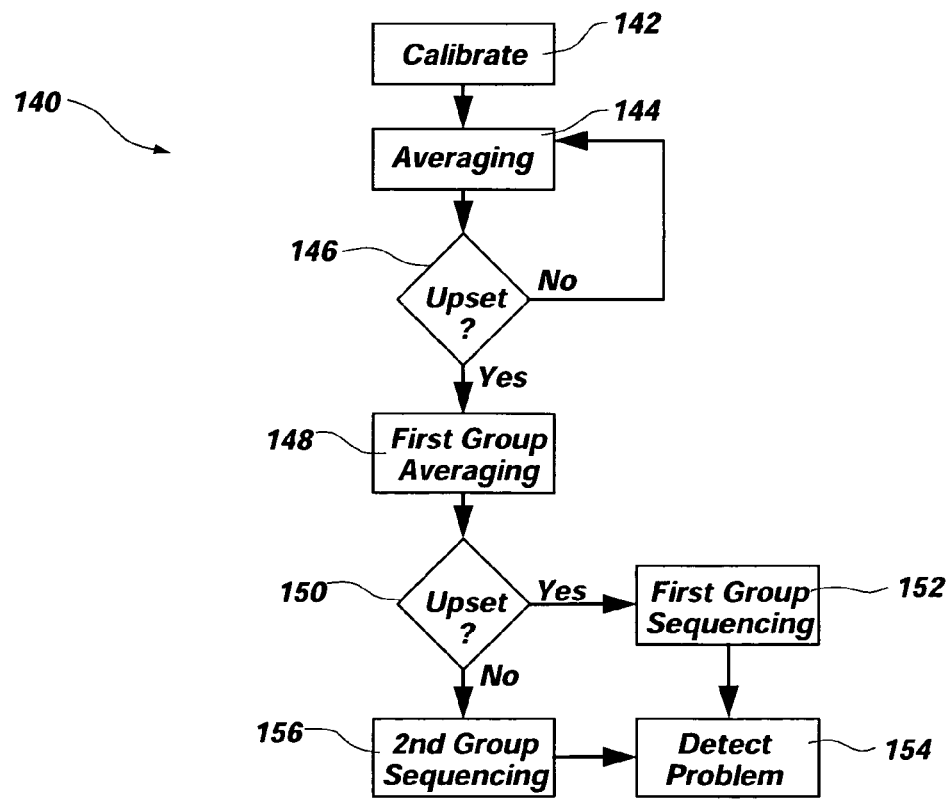
Figure 8:
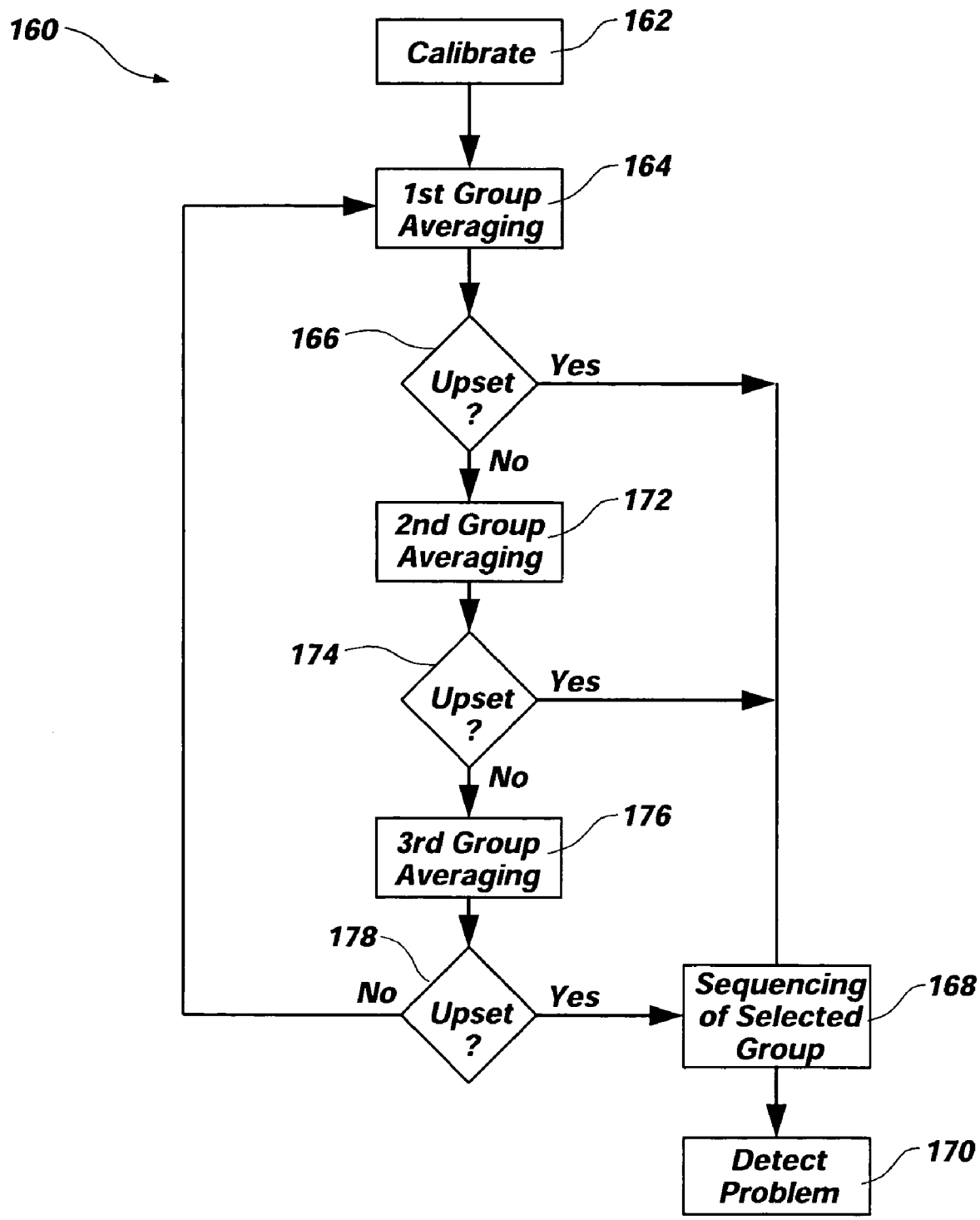

Referring now to FIGS. 6, 7 and 8, flow diagrams are provided showing methods carried out by the sequencing and averaging apparatus of the embodiments disclosed herein. The flow diagrams represent algorithms that may be programmed in software or firmware in the programmable logic controller 80. As shown in FIG. 6, a system 120 is shown with multiple sources to be sampled. The programmable logic controller 80 is initially calibrated, at step 122, for each valve 31–34 by pumping a calibration fluid through each sampling source and each valve to establish a flow rate and other parameters for each valve. In situations involving gas testing, a typical calibration gas might be sulfur dioxide or nitrogen oxide having nitrogen gas doped with the impurity to be tested. During calibration, the flow rate is determined for of each source being monitored, for a purpose to be discussed below.

Next, at step 124, the system is operated in an averaging mode in the programmable logic controller 80 actuates each of the valves 31–34 to provide samples to the manifold 20 from each of the sources to be monitored. The samples are mixed to form an average test sample, which is sent to the analyzer 70 to be tested for the presence of a predetermined parameter. The averaging mode can be carried out in at least two different ways. The valves may be rapidly sequenced to provide samples from each source that are mixed in the manifold to form an average test sample. Alternately, the valves may be turned on simultaneously during a sampling period to provide samples that are mixed in the manifold to form an average test sample.

In either averaging sampling process, the valves may be actuated for different time periods, depending on the flow rate of each source being sampled. For example, if the flow rate of the sample obtained from valve 31 is twice the flow rate of the sample obtained from valve 32, the sample time for valve 31 may be half of the sample time of valve 32. In this manner, the same amount of each monitored sample is mixed in the manifold to obtain a true average test sample.

For example, in the sequential averaging process, a sample time of one second might be used. During that one-second sample time each valve is sequenced for a different fraction of one second corresponding to the ratio of the flow rate of the respective monitored source relative to a standard flow rate. Similarly, in the simultaneous averaging process, each valve may be actuated at the beginning of the one-second sample period. Then, each valve shuts off at the end of a predetermined fraction of the sample period, depending on the flow rate of the respective source being sampled. Sampling periods during the averaging mode may fall within a range of 1/5 seconds to 5 seconds. It is important to maintain the averaging mode sampling times relatively short, in order to provide a true average test sample in a relatively small manifold chamber volume and to quickly detect an upset condition.

Next, at step 126, analyzer 70 tests the average sample for an upset condition. If no upset condition is detected, the averaging mode of sampling is continued. If an upset condition is detected, the programmable logic controller 80 switches over to a sequencing mode, as shown at step 128, to detect the problem valve, at step 130, that is sampling a problem source. In this mode, the programmable logic controller 80 sequentially actuates each valve 31–34 for a period long enough to provide a test sample in the manifold 20 that can be sent to the analyzer 70 for testing. A typical sample time during the sequencing mode is 15 seconds. The sample time may vary over a wide range of as much as 10 seconds to 5 minutes, depending on the flow rates and the length of sample line of the sources being sampled.

Looking now at FIG. 7, an alternate method is shown for operating the sequencing and averaging system of the present embodiments. The method shown in FIG. 7 is helpful, in situations, such as system 140, where there are a large number of valves sampling a large number of sources. At step 142, the programmable logic controller 80 is calibrated for each of the valves 31–34, as previously discussed. At step 144, the system is operated initially in the averaging mode and continues in that mode until an upset condition is detected, at step 146.

At the time of upset condition detection, the programmable logic controller 80 divides the sampling valves into two equal groups. At step 148, an averaging mode operation may then be carried out for the first group in which samples from each source in the group are mixed in the manifold 20 to form a first group test sample. This sample is then tested by the analyzer 70, at step 150, to determine whether the upset condition is in the first group. If so, the valves of the first group are sequentially sampled, at step 152, to detect the problem sample source, as shown at step 154. If the first group does not show an upset condition, then the problem is in the second group. Accordingly, as shown at step 156, the second group is sequentially sampled to detect the problem sample source. It should be understood that the sampling valves may be divided in any number of groups to carry out the dividing process shown in FIG. 7. If more than two groups are selected, then additional averaging mode testing must be carried out to find the problem.

FIG. 8 shows one example of a system 160 having multiple groups involving a large number of valves and sources. In this situation, it might not be practical to average samples from all of the sources, as was done with systems 120 and 140 in FIGS. 6 and 7. Rather, after the calibration step 162, the system might be separated into multiple groups, such as first, second and third groups shown. Then the system may be sequenced through each of the average samples of the groups to determine whether an upset condition had occurred. If so, then sequencing may be used to locate the problem.

Thus, at step 164, the first group is averaged and the output sampled. If an upset condition is detected, at step 166, the first group is selected for sequencing, at step 168, to detect a problem, at step 170. If an upset condition is not detected at step 166, the second group is averaged and the output sampled, at step 172. If an upset condition is detected, at step 174, the second group is selected for sequencing, at step 168. If an upset condition is not detected, at step 174, the third group is averaged and the output sampled, at step 176. If an upset condition is detected, at step 178, the third group is selected for sequencing, at step 168. If an upset condition is not detected at step 178, the system sampling returns to the first group at step 164.

In other situations, a system might be initially sequenced in a calibration mode to calibrate each valve. In the event that a valve is found to be out of calibration, an adjustment is made. The system may continue to sequence in the calibration mode until no calibration problems are detected or for a safe period of time, after which the system may go into a normal sampling process, such as those shown in FIGS. 6, 7 and 8.

For example, in a large boiler, several dampers may control the fuel-air mixture in various parts of the boiler. In the event that too little air is found to be going to a burner, the respective damper may signal an out-of-calibration condition, at which time the damper position may be changed to allow more air to the burner. After the dampers are all in calibration, or after a safe period of time, such as twenty minutes, the system may go into an averaging mode, pending the detection of an upset condition.

Figure 9:
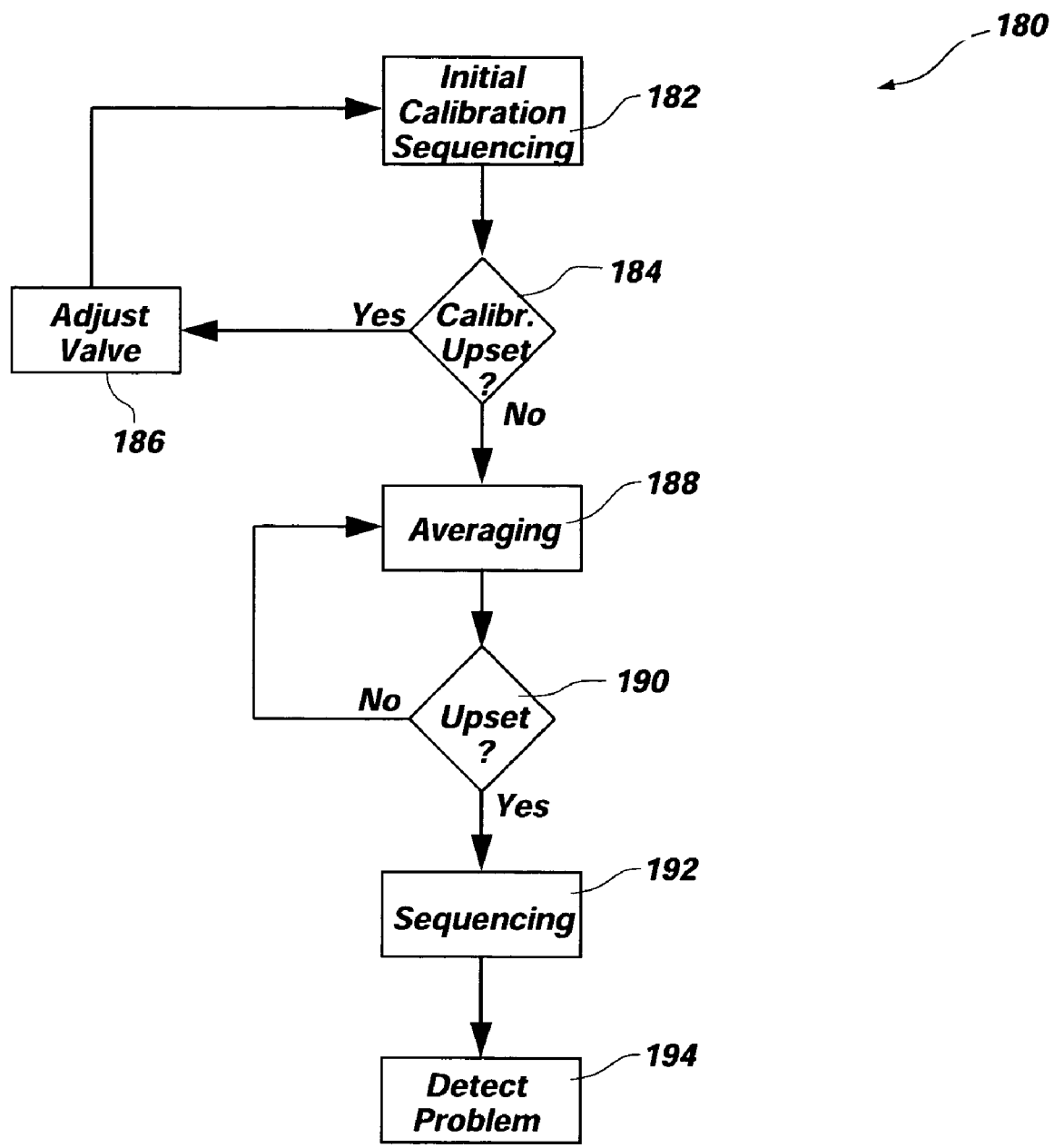

FIG. 9 shows an example of such a system 180. At step 182, the system conducts a calibration sequencing through each valve or damper to determine whether a valve is out of calibration. If a calibration problem is detected, at step 184, the appropriate valve is adjusted to correct the problem, at step 186. The system 180 then continues at step 182 with its initial calibration sequencing. After calibration has been completed, the system 180 moves on to an averaging step 188, until an upset condition is detected, at step 190. Then, at step 192. the system sequences through each valve until a problem is detected at step 194.

While this disclosure has been described as having preferred embodiments, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. Apparatus for testing and analyzing a plurality of stream sources having various flow rates to monitor for an upset condition in one of the stream sources, comprising:
   (a) a manifold adapted to form a test sample of one or more of the plurality of stream sources;
   (b) a plurality of sampling devices for sampling the plurality of stream sources, each sampling device being coupled to the manifold to provide a stream sample from one of the stream sources to the manifold;
   (c) a controller in electronic communication with each of the plurality of sampling devices for providing test samples in the manifold, the controller alternately operating the sampling devices in (1) a sequencing mode in which each test sample is a stream sample from one of the plurality of sampling devices and (2) an averaging mode in which each test sample is representative of an average of the stream samples from the plurality of sampling devices; and (d) an analyzer coupled to the manifold to receive the test samples from the manifold and analyze each test sample to determine the presence of the upset condition.

2. The apparatus of claim 1, wherein the controller operates the sampling devices in the averaging mode by providing simultaneous stream sample inputs in the manifold from the plurality of sampling devices that are mixed to provide a test sample.

3. The apparatus of claim 1, wherein the controller operates the sampling devices in the averaging mode by providing sequential stream sample inputs in the manifold from the plurality of sampling devices that are mixed to provide a test sample.

4. The apparatus of claim 3, wherein the controller operates the sampling devices in the averaging mode for a selected period of time for each of the plurality of sampling devices, the period of time being representative of a flow rate for the each of the respective stream sources being sampled.

5. The apparatus of claim 1, wherein the plurality of sampling devices each includes a solenoid valve.

6. The apparatus of claim 5, wherein the plurality of solenoid valves are each three-way valves having an input port coupled to one of the stream sources and an outlet port to the manifold.

7. The apparatus of claim 6, wherein each of the three-way valves has a bypass port coupled to a bypass line for drawing a continual stream from each of the plurality of solenoid valves to an output vent.

8. The apparatus of claim 1, wherein the controller is selected from a group consisting of a programmable logic controller, distributed control system and computer.

9. The apparatus of claim 1, wherein the controller is adapted to operate in the averaging mode during normal operation of the apparatus.

10. The apparatus of claim 1, wherein the controller is adapted to operate in the sequencing mode when an upset condition is detected, in order to sequentially determine which of the plurality of samples is in an upset condition.

11. The apparatus of claim 10, wherein the controller is adapted to operate in a first portion averaging mode, in which only a first portion of the plurality of sampling devices are actuated when an upset condition is detected.

12. The apparatus of claim 11, wherein the controller is adapted to operate in a second portion averaging mode, in which only a second portion of the plurality of sampling devices are actuated when a upset condition is not detected in the first portion.

13. The apparatus of claim 11, wherein the controller is adapted to operate in a sequencing mode, in which only the first portion of the plurality of sampling devices are sequentially actuated when an upset condition is detected in the first portion.

14. Apparatus for testing and analyzing a plurality of stream sources having various flow rates to monitor for an upset condition in one of the stream sources, comprising:
(a) a manifold adapted to form test samples from the plurality of stream sources;
(b) a plurality of sampling devices for sampling the plurality of stream sources, each sampling device being coupled to the manifold to provide sequential samples from the stream sources to the manifold;
(c) a sequencer coupled to each of the plurality of sampling devices to sequentially activate the plurality of sampling devices, the sequencer operating alternately in a first sequencing mode and a second sequencing mode;
(d) an analyzer coupled to the outlet to analyze the test samples in the manifold for a selected parameter to determine the presence of the upset condition; and
(e) wherein the sequencer operates in the first sequential mode to sequentially actuate the sampling devices at a rate fast enough to provide a sequence of test samples for mixing in the manifold, each test sample being representative of an average mixture of samples from all of the plurality of sampling devices.

15. The apparatus of claim 14, wherein the sequencer operating in the first sequential mode to sequentially actuate each of the sampling devices for a period of time corresponding to a flow rate for the respective stream source being sampled.

16. Apparatus for testing and analyzing a plurality of stream sources having various flow rates to monitor for an upset condition in one of the stream sources, comprising:
(a) a manifold adapted to form test samples from the plurality of stream sources;
(b) a plurality of sampling devices for sampling the plurality of stream sources, each sampling device being coupled to the manifold to provide sequential samples from the stream sources to the manifold;
(c) a sequencer coupled to each of the plurality of sampling devices to sequentially activate the plurality of sampling devices, the sequencer operating alternately in a first sequencing mode and a second sequencing mode;
(d) an analyzer coupled to the outlet to analyze the test samples in the manifold for a selected parameter to determine the presence of the upset condition; and
(e) wherein the sequencer operates in the second sequential mode to sequentially actuate the sampling devices at a rate slow enough to provide a discrete sequence of test samples in the manifold, each test sample being representative of a sample from one of the stream sources.

17. A method for testing and analyzing a plurality of stream sources having various flow rates to monitor for an upset condition in one of the stream sources, comprising:
(a) providing a plurality of samples from the plurality of stream sources using a plurality of sampling devices coupled to a manifold;
(b) providing test samples in the manifold using a controller in electronic communication with the plurality of sampling devices by alternately operating the plurality of sampling devices in (1) a sequencing mode in which each test sample is a stream sample from one of the plurality of sampling devices and (2) an averaging mode in which each test sample is representative of an average of the stream samples from the plurality of sampling devices; and
(c) analyzing the test samples using an analyzer coupled to the manifold to determine the presence of the upset condition.

18. The method of claim 17, wherein the controller operates the sampling devices in the averaging mode by providing simultaneous stream sample inputs in the manifold from the plurality of sampling devices that are mixed to provide the test sample.

19. The method of claim 17, wherein the controller operates the sampling devices in the averaging mode by providing sequential stream sample inputs in the manifold from the plurality of sampling devices that are mixed to provide the test sample.

20. The method of claim 17, wherein the controller operates the sampling devices in the averaging mode for a selected period of time for each of the plurality of sampling devices that is representative of a flow rate for the each of the respective stream sources being sampled.

21. The method of claim 17, further comprising adapting the controller to operate the sampling devices in the averaging mode during normal operation of the apparatus.

22. The method of claim 17, further comprising adapting the controller to operate the sampling devices in the sequencing mode when an upset condition is detected, in order to sequentially determine which of the plurality of samples is in an upset condition.

23. The method of claim 17, further comprising adapting the controller to operate the sampling devices in the averaging mode, in which only a first portion of the sampling devices are actuated when an upset condition is detected.

24. The method of claim 23, further comprising adapting the controller to operate the sampling devices in the averaging mode, in which only a second portion of the sampling devices are actuated when an upset condition is not detected in the first portion.

25. The method of claim 23, further comprising adapting the controller to operate the sampling devices in the sequencing mode, in which only the first portion of the sampling devices are sequentially actuated when an upset condition is detected in the first portion.

26. A method for testing and analyzing a plurality of stream sources having various flow rates to monitor for an upset condition in one of the stream sources, comprising:

(a) providing a manifold adapted to form test samples from at least a first group of the plurality of stream sources;

(b) providing samples from the stream sources to a plurality of actuable sampling devices for sampling at least the first group of the plurality of stream sources;

(c) actuating at least one of the plurality of sampling devices to provide a sample to the manifold using a controller coupled to each of the plurality of sampling devices, the controller operating alternately in an averaging mode and a sequencing mode; and (d) analyzing the test sample in the manifold for a selected parameter to determine the presence of the upset condition.

27. The method of claim 26 further comprising adapting the controller to sequentially sample a plurality of groups of sampling devices operating in the averaging mode, each group being associated with a corresponding group of stream sources.

28. The method of claim 27, further comprising adapting the controller to operate the sampling devices of a selected group in the sequencing mode when an upset condition is detected in the selected group, in order to sequentially determine which of the plurality of samples in the selected group is in an upset condition.

29. The method of claim 26 comprising operating the controller in the sequencing mode initially to calibrate the plurality of acutable sampling devices.

* * * * *